(12) United States Patent
Norman et al.

(10) Patent No.: US 7,208,186 B2
(45) Date of Patent: Apr. 24, 2007

(54) CHEWING GUM FORMULATION AND METHOD OF MAKING THE SAME

(75) Inventors: Gary T. Norman, Middletown, DE (US); Arun F. Amin, Wilmington, DE (US)

(73) Assignee: SPI Pharma, Inc., New Castle, DE (US)

( * ) Notice: Subject to any disclaimer, the term of this patent is extended or adjusted under 35 U.S.C. 154(b) by 44 days.

(21) Appl. No.: 10/422,502

(22) Filed: Apr. 24, 2003

(65) Prior Publication Data

US 2004/0013767 A1   Jan. 22, 2004

Related U.S. Application Data

(63) Continuation-in-part of application No. 10/245,419, filed on Sep. 17, 2002, now abandoned.

(60) Provisional application No. 60/323,398, filed on Sep. 18, 2001.

(51) Int. Cl.
   *A23G 4/08*   (2006.01)

(52) U.S. Cl. .................. 426/3; 426/5; 424/48; 424/440; 424/441

(58) Field of Classification Search .................... 426/3, 426/5, 143, 285, 453; 424/48, 440, 441
   See application file for complete search history.

(56) References Cited

U.S. PATENT DOCUMENTS

| | | | |
|---|---|---|---|
| 2,290,120 A | | 7/1942 | Thomas |
| 3,262,784 A | * | 7/1966 | Bucher ........................ 426/5 |
| 4,000,321 A | | 12/1976 | Mochizuki et al. |
| 4,161,544 A | * | 7/1979 | Kaul ............................ 426/5 |
| 4,370,350 A | | 1/1983 | Fisher et al. |
| 4,405,647 A | * | 9/1983 | Fisher et al. ................. 426/4 |
| 4,737,366 A | | 4/1988 | Gergely et al. |
| 4,741,905 A | | 5/1988 | Huzinec |
| 4,753,805 A | * | 6/1988 | Cherukuri et al. ............ 426/5 |
| 5,711,961 A | | 1/1998 | Reiner et al. |
| 5,824,291 A | | 10/1998 | Howard |
| 5,866,179 A | | 2/1999 | Testa |
| 6,582,738 B2 | * | 6/2003 | Gubler ......................... 426/5 |
| 6,767,567 B1 | * | 7/2004 | Douaire et al. ............... 426/75 |
| 2005/0074518 A1 | | 4/2005 | Soldani |

FOREIGN PATENT DOCUMENTS

| | | | |
|---|---|---|---|
| EP | 0 151 344 A | | 8/1985 |
| EP | 0214834 | * | 3/1987 |
| EP | 0 298 922 A | | 1/1989 |
| EP | 0 399 479 A | | 11/1990 |
| WO | WO-97/21424 A | | 6/1997 |
| WO | 99/66905 | * | 12/1999 |
| WO | WO-00/56281 A | | 9/2000 |
| WO | WO-02/078459 A1 | | 10/2002 |

OTHER PUBLICATIONS

Sangalli et al, "Inert Monolithic Device with a Central Hole for Constant Drug Release", European Journal of Pharmaceutics,40(1994)Dec., No. 6, Stuttgart, Germany.*
Patent abstracts of Japan, vol. 1995, No. 06, Jul. 31, 1995 & JP 07 067541 A (Korisu KK), Mar. 14, 1995, abstract.
English language abstract for EP 0 399 479 (Nov. 28, 1990).
Chewing & Bubble Gum Workshop Presentation; National Confectioners Association; Doug Fritz et al., Apr. 2-4, 2001.

* cited by examiner

*Primary Examiner*—Arthur L. Corbin
(74) *Attorney, Agent, or Firm*—Connolly Bove Lodge & Hutz LLP

(57) ABSTRACT

The present invention involves a novel chewing gum formulation and a method of making the same. The chewing gum formulation is used to form a final chewing gum composition which contains an active ingredient which is released from the chewing gum as the gum is masticated in the mouth of the user. The chewing gum made from the chewing gum composition of the present invention is initially a compressed body, such as a tablet, which quickly dissociates into a multiplicity of small pieces upon initial chewing followed by a reformation of the pieces into a coherent mass of chewing gum after a few seconds of chewing. Both the chewing gum formulation and the chewing gum composition are in the form of a free-flowing particulate which is capable of being directly compressed at high speed by a standard tableting machine into chewing gum tablets.

22 Claims, No Drawings

US 7,208,186 B2

CHEWING GUM FORMULATION AND METHOD OF MAKING THE SAME

CROSS-REFERENCE TO RELATED APPLICATION

The present patent application is a continuation-in-part of U.S. patent application Ser. No. 10/245,419 filed on Sep. 17, 2002, now abandoned, and claims the benefit of the filing date of U.S. provisional application No. 60/323,398 filed on Sep. 18, 2001.

BACKGROUND OF THE INVENTION

A. Field of the Invention

The present invention involves a novel chewing gum formulation and a method of making the same. The chewing gum formulation is used to form a final chewing gum composition which contains an active ingredient which is released from the chewing gum as the gum is masticated in the mouth of the user. The chewing gum made from the chewing gum composition of the present invention is initially a compressed body, such as a tablet, which, in certain embodiments of the present invention, quickly dissociates into a multiplicity of small pieces upon initial chewing followed by a reformation of the pieces into a coherent mass of chewing gum after a few seconds of chewing. Both the chewing gum formulation and the chewing gum composition are in the form of a free-flowing particulate which is capable of being directly compressed at high speed by a standard tableting machine into chewing gum tablets.

B. Description of the Related Art

The prior art methods of producing compressible chewing gums involved one of the two techniques described below.

The first technique was to freeze the gum base or mixtures containing the gum base and then grind or otherwise comminute the frozen materials to obtain a particulate material containing the gum base. This particulate material could then be mixed with other materials (usually in particulate form) to create a compressible chewing gum. Some of the U.S. patents describing this technology are U.S. Pat. Nos. 2,290,120; 4,737,366; 5,711,961 and 5,866,179.

The second technique was to mix a dry powder (usually the sweetener) into a molten gum base while subjecting the mixture to shear (i.e., through the mixing force) and cooling. This technique causes the comminution of the mixture as the plasticity of the mixture decreases and the mixture becomes more rigid due to the effects of cooling and the addition of the dry particulate material. The primary U.S. patent describing this technique is U.S. Pat. No. 3,262,784, which is discussed in more detail below.

U.S. Pat. No. 3,262,784 describes a compressible chewing gum product and a method of producing the same. The compressible chewing gum product is a free-flowing particulate at room temperature which can be shaped by simple compression or blended with other finely-divided materials or with liquid materials. The chewing gum is formed by heating a chewing gum base until it is molten and then slowly mixing into the molten gum base dry, finely-divided sugar without adding any additional heat to the molten mass during the mixing step, until the sugar is completely dispersed in the chewing gum base. By the time all of the sugar has been mixed into the chewing gum base, the product is in the form of a non-tacky, friable mass, which due to the mixing operation, exists as chunks, lumps, granules and particles of widely varying size.

It is disclosed in this patent that the gum base must be molten when the sugar is first mixed with the gum base and that the chewing gum base cannot be added to the sugar (i.e., the order of addition of the components is essential). Further, the product that is obtained from the mixer, although non-tacky and friable, has a widely varying particle size.

Additional variations on the above-described prior art processes can be found in the patents discussed below.

U.S. Pat. No. 4,161,544 describes a process for making a pourable material for chewing gum that is supposed to be an improvement over the process described in U.S. Pat. No. 3,262,784. The process of this patent involves heating a dry base material to 60° to 120° C. and adding thereto dry sugar materials; polysaccharides; natural gums and swelling agents, mixing the ingredients at 60° to 120° C. for about 1–15 minutes, thereafter cooling the mixture to about 30° to minus 5° C. and continuing the mixing operation for another 1–15 minutes. This process is described as providing a pourable powder which can be compressed to desired shapes after being passed through a screen having a mesh size of about 1 mm.

U.S. Pat. No. 4,753,805 describes a process of producing a chewing gum tablet having a water content of about 2 to about 8% which involves forming a chewing gum composition by standard techniques (i.e., by mixing the secondary ingredients into a melted blend of the gum base and the sweetener until a homogeneous blend is obtained and then cooling the molten mixture until solid) and then grinding the chewing gum composition in the presence of a grinding aid to comminute the chewing gum composition. The comminuted chewing gum composition is then mixed with a compression aid, which is usually composed of several ingredients that have different functions (e.g., lubricants, glidants, and anti-adherents) and the final mixture is tableted.

SUMMARY OF THE INVENTION

One of the objects of the present invention is to provide a chewing gum composition, comprising a chewing gum formulation and an active ingredient, that is directly compressible at high speed on a standard tableting machine to form chewing gum tablets.

Another object of the present invention is to provide a chewing gum, in the form of a compressed tablet, which is capable of rapidly releasing an active ingredient into the mouth of the user. The terms "rapid release" and "rapidly released", as used in the present patent application, mean that at least 50 to 75% by weight, preferably at least 70 to 80% by weight, of the active ingredient is released to the saliva in the mouth of the user within from thirty seconds to five minutes (preferably from thirty seconds to three minutes, most preferably from 1 to 3 minutes) of the initial chew under normal chewing conditions of about one chew per second.

Another object of the present invention is to provide a method of making a chewing gum formulation which can be used to produce a chewing gum composition having the above-described properties which does not involve: a) the careful addition of the sweetener and secondary ingredients to an initial melt of the gum base; or b) subjecting the gum base or chewing gum formulation to cold temperatures to form a friable mass.

These and other objects and advantages of the present invention can be appreciated by referring to the following description or may be learned by the practice of this invention.

The chewing gum formulation of the present invention is a free-flowing particulate which is capable of being directly compressed at high speed by a standard tableting machine into chewing gum tablets that provide a quick dissociation of the chewing gum into a multiplicity of small pieces upon initial chewing (i.e., the chewing gum tablet begins to dissociate on the first chew and reaches maximum dissociation in about two to twenty chews, preferably reaching maximum dissociation in about two to ten chews) followed by a reformation of the pieces into a coherent mass of chewing gum after a few seconds of active chewing (i.e., reformation in about 1 to 20 seconds after achieving the maximum dissociation of the chewing gum tablet, preferably in about 2 to 10 seconds after achieving the maximum dissociation of the chewing gum tablet, assuming one chew per second). These results are achieved through the use of a combination of ingredients that can be processed to a directly compressible particulate without the careful addition of the sweetener and secondary ingredients to an initial melt of the gum base or the use of cold temperatures to make the gum base or formulation friable or the use of a grinding aid to enable the comminution of the chewing gum formulation or composition.

When the chewing gum formulation is mixed with an active ingredient to form a chewing gum composition, the chewing gum composition should also be capable of being directly compressed at high speed by a standard tableting machine into chewing gum tablets that provide a quick dissociation of the chewing gum into a multiplicity of small pieces upon initial chewing followed by a reformation of the pieces into a coherent mass of chewing gum after a few seconds of chewing.

Before the addition of the active ingredient and the compression step, the chewing gum formulation of the present invention is in a free-flowing particulate form and comprises the following ingredients:
 a) a gum base;
 b) a granulating agent;
 c) a processing aid; and, optionally,
 d) a sweetening agent.

In addition, one or more flavoring or coloring agents can be added to the chewing gum formulation, during or after the production of the chewing gum formulation. Usually, the one or more flavoring or coloring agents are mixed with the chewing gum formulation during the production of the chewing gum composition. In addition, one or more common lubricants (e.g., magnesium stearate, sodium stearyl fumarate, hydrogenated vegetable oils, talc and stearic acid) are added to either the chewing gum formulation or the chewing gum composition to aid in the tableting of the formulation or composition. In any event, the lubricants are added to the formulation or composition before tableting. The lubricants are added in an amount of from 1 to 8% by weight, preferably from 1 to 5% by weight, most preferably from 1 to 3% by weight of the chewing gum formulation or composition.

In one embodiment of the present invention, at least one active ingredient is added to the chewing gum formulation to form a chewing gum composition which is then subjected to compression to form chewing gum tablets.

In another embodiment of the present invention, chewing gum tablets are formed directly from the chewing gum formulation and one or more active ingredients are then applied to the surface of the chewing gum tablets (e.g., by dip or spray coating techniques). In this embodiment of the present invention, one or more flavoring or coloring agents can also be applied to the surface of the chewing gum tablets, either simultaneously with the one or more active ingredients or in one or more separate steps.

The gum base can be any gum base that can be uniformly distributed as small particles (liquid or solid) throughout the chewing gum formulation when the gum base is mixed with the other components of the chewing gum formulation in a mixing apparatus. It is preferred that the gum base be in solid form and friable (i.e., when subjected to the mixing action in the mixing apparatus) at the time it is added to the mixing apparatus in which it will be mixed with the other components of the chewing gum formulation. In a preferred embodiment of the present invention, the gum base is (or can be made into) a free-flowing (non-tacky) particulate at temperatures in the range of from about 10° C. to about 35° C. The term "gum base", as used herein, means either one or more pure gums without any additives or blends of one or more pure gums and one or more additives (e.g., those that are sold commercially as gum bases for chewing gum).

The granulating agent can be one or more substances that do not adversely react with the other components of the chewing gum composition and/or the active ingredient(s) and result in a chewing gum formulation and/or chewing gum composition with the aforementioned properties when mixed with the other components according to the process of the present invention. The granulating agent is preferably water-soluble so that the final chewing gum product will have better organoleptic properties. The granulating agent may also function as a sweetening agent, as discussed below.

The sweetening agent can be one or more sweeteners of any type as long as the sweeteners do not adversely react with the other components of the chewing gum composition and/or the active ingredient(s) and, when used in the method of the present invention, form a chewing gum formulation and/or chewing gum composition with the aforementioned properties. Examples of potential sweeteners for use in the chewing gum formulation of the present invention are carbohydrates, particularly sugars such as sucrose, dextrose and glucose, polyols (e.g., sorbitol, mannitol, maltitol, xylitol, isomalt and erythritol), glycine, aspartame, cyclohexyl sulfamate, saccharine, acesulfame K, stevioside and ammonium glycyrrhizinate. The sweetening agent is preferably added as a dry particulate or powder. Preferred sweeteners are sugars, such as sucrose or dextrose, and polyols, such as sorbitol, mannitol or isomalt.

Certain substances can function as both a sweetening agent and a granulating agent (e.g., sugars, such as sucrose, fructose and dextrose, and polyols, such as sorbitol, mannitol or isomalt). When one or more of these substances is used in the chewing gum formulation and/or composition as a granulating agent, there may be no need for a separate or different sweetening agent.

In a highly preferred embodiment of the present invention, sorbitol is used as a granulating agent which also contributes to the sweetness of the final chewing gum product. In this embodiment of the present invention, the amount of sorbitol present is from 10–90.9% by weight, preferably from 45 to 90.9% by weight, of the chewing gum formulation.

The processing aid can be one or more substances that help to keep the chewing gum formulation in free-flowing particulate form, both during the formation of the chewing gum formulation and afterwards. Further, the presence of the processing aid may also result in a chewing gum formulation and/or composition that is less sticky, which reduces the amount of the chewing gum formulation that sticks to the interior surfaces and blades of the mixing equipment and therefore remains inside the mixing equipment after each production run. By reducing the amount of the chewing gum formulation that remains inside the mixing equipment after each production run, the yield of chewing gum formulation from each production run is increased (e.g., yields of chewing gum formulation of 85% to 90%, preferably from 90% to 95%, or even higher, are obtained). Further, the mixing equipment can be cleaned more easily and thoroughly, thereby resulting in less down time between production runs. These advantages also apply to the mixing equipment used to produce the chewing gum composition (e.g., there is less material sticking to the interior surfaces and moving parts of the mixing equipment so the equipment can be cleaned more easily and thoroughly than with other chewing gum formulations). The ability to easily and thoroughly clean the mixing equipment between production in a simple and cost-effective manner results in a process which should be acceptable under the cGMP guidelines of the United States Food and Drug Administration (FDA) (e.g., by preventing cross-contamination of active ingredients).

By reducing the stickiness of the chewing gum composition, the processing aid also contributes to the ability of the chewing gum composition to be directly compressed at high speed on a standard tableting machine, by reducing or eliminating the tendency of the chewing gum formulation to stick to the punches and dies of the tableting machine.

The superior compaction properties of the chewing gum formulations and chewing gum compositions of the present invention permit these formulations and compositions to be easily compressed into tablets having a variety of shapes (e.g., complex shapes such as animal figures) and sizes. In one embodiment of the present invention, the chewing gum tablets are produced with a hole (hereinafter referred to as the "through-hole") that passes through the tablet. Although the through-hole in the tablet does not have to be located in the center of the tablet, applicants have found this to be a desirable location for the through-hole. Further, it is preferred that the through-hole is formed during the compression step of the tablet production process and is not formed by punching or drilling the tablet after compression. The through-hole passes from one face of the tablet to the opposite face and has a usual cross-sectional diameter or width of from 1 mm to 20 mm. For most tablets, the maximum diameter or width of the through-hole is ¾ (or 75%) of the maximum diameter or width of the tablet through which the through-hole passes. In another embodiment of the present invention, after a gum tablet with a through-hole has been formed, the through-hole may be completely or partially filled with a composition that contains one or more substances that are not contained in the remainder of the gum tablet. For example, the composition located in the through-hole of the chewing gum tablet may contain an active ingredient and/or flavor that are/is not contained in the remainder of the chewing gum tablet. In this embodiment of the present invention, the composition located in the through-hole of the tablet may, inter alia, affect the flavor or texture of the tablet and/or may provide one or more active ingredients to the user (i.e., the individual who is chewing the tablet) that would not be provided by the chewing gum tablet alone.

Examples of preferred processing aids are silica and silicate substances such as talc, silica gel, precipitated silica, fumed silica and colloidal silica. In a highly preferred embodiment of the present invention, the processing aid consists essentially of silica gel.

The chewing gum formulation is produced by adding the gum base, in the form of a solid particulate, to a mixture of the granulating agent and at least a portion of the processing aid that is being mixed within a mixer. The particles of the gum base are allowed to mix with the mixture of the granulating agent and the processing aid for a time while the temperature in the mixer is below the melting point of the gum base. The temperature in the mixer is then increased to a temperature which is sufficient to melt at least the surface of the gum base particles and the contents of the mixer are mixed for several minutes at this temperature to obtain a uniform mixture of the gum base, the granulating agent and the processing aid. This uniform mixture is in particulate form (i.e., granules) inside the mixer It is preferred that a portion of the processing aid is added to the mixer after this uniform mixture is obtained and allowed to mix with the uniform mixture particles for a short time so that the processing aid can form a partial coating on the uniform mixture particles before the contents of the mixer are removed from the mixer.

As the gum base, granulating agent and processing aid are mixed in the mixing device, they may, for a time, form a doughy or plastic mass that is not in particulate form. In this situation, the mixer can be outfitted with choppers that break up the doughy or plastic mass and form particles that are then removed from the mixer. Alternatively, the mixture can be removed from the mixer in the form of a doughy or plastic mass and subjected to a subsequent comminution step to form a free-flowing particulate. In any event, the chewing gum formulation may be subjected to a comminution or screening step before use to create or obtain particles of a desired size. -However, it is not necessary or desirable to subject the chewing gum formulation to temperatures below normal room temperature (20 to 30° C. or 68 to 86° F.) for the purpose of rendering the formulation friable. Such a step, if performed, would be an additional or extra step which is not necessary to make the chewing gum formulation friable so that it can be comminuted to a free-flowing particulate form.

If a sweetening agent is used to produce the chewing gum tablets of the present invention, the sweetening agent may be added to the mixer during the production of the chewing gum formulation. Alternatively, the sweetening agent may be mixed with the chewing gum formulation during the production of the chewing gum composition. In certain embodiments of the present invention, the sweetening agent may even be applied to the chewing gum tablets during or after the compression step. The timing of the addition of the sweetening agent depends primarily on the identity and properties of the sweetening agent. For example, if the sweetening agent is a bulk sweetener, such as sugar or a polyol, at least a portion of the sweetening agent will be added during the production of the chewing gum formulation, usually before the addition of the gum base. If the sweetening agent is an intense sweetener, such as aspartame or saccharine, then at least a portion of the sweetening agent (usually all of the sweetening agent) will be mixed with the chewing gum formulation during the production of the chewing gum composition or added to the chewing gum composition after it has been produced. When a combination of one or more bulk sweeteners and one or more intense sweeteners are used as the sweetening agent, then the bulk sweetener(s) is(are) usually added to the mixer during the production of the chewing gum formulation (usually before the addition of the gum base) and the intense sweetener(s) is(are) usually mixed with the chewing gum formulation during the production of the chewing gum composition or added to the chewing gum composition after it has been produced.

When the substance or substances used as the granulation agent are also used as the sweetening agent, then the total amount of the substance or substances in the chewing gum formulation is usually from 45 to 90.9% by weight, preferably from 55 to 85% by weight, most preferably from 60 to 80% by weight. When the sweetening agent is not also the granulating agent or one of the granulating agents or is added to supplement the sweetening effect provided by a substance that also functions as a granulating agent, then the amount of the sweetening agent (or supplemental sweetening agent) is usually from 0.1 to 45% by weight of the chewing gum formulation or from about 0.1 to 40% by weight of the chewing gum composition. When both a sweetening agent and a granulating agent are used, it may be desirable to limit the maximum amount of granulating agent to 90.8% by weight of the chewing gum formulation.

In one embodiment of the present invention, a chewing gum composition is formed by mixing the chewing gum formulation, in the form of a free-flowing particulate, with at least one active ingredient. When the active ingredient(s) is(are) in particulate form, it(they) is(are) dry-mixed with the chewing gum formulation to form the chewing gum composition. When the active ingredient(s) is(are) in the form of a suspension or solution of the active ingredient(s) in a liquid (e.g., water), the solution or suspension containing the active ingredient(s) is contacted with the chewing gum formulation in such a manner that an amount of the active ingredient(s) is(are) deposited on the surface of the chewing gum formulation particles or inside any porosity that may be present in the particles, and then the particles are dried, if necessary (e.g., by evaporation), to form the chewing gum composition particles that are then compressed to form chewing gum tablets. The solution or suspension containing the active ingredient(s) may be contacted with the chewing gum formulation particles in any manner (e.g., by dipping the formulation into the solution or suspension or by spraying the solution or suspension onto the formulation) and any number of times, to form the final chewing gum composition.

The active ingredient(s) may also be added to the chewing gum formulation as both a dry particulate and as a solution or suspension in a liquid. For example, when only one active ingredient is to be added to the chewing gum formulation, a portion of the active ingredient may be added as a dry particulate in one step and a portion of the active ingredient may be added as a solution or suspension in another step. When more than one active ingredient is to be added to the chewing gum formulation, one or more of the active ingredients may be added as a dry particulate and one or more of the active ingredients may be added as a solution or suspension.

When the active ingredient is added to the chewing gum formulation and the chewing gum formulation is in the form of a particulate or powder, most or all of the active ingredient is loosely bound to the outer surfaces of the particles of the chewing gum formulation (e.g., especially when the active ingredient is in the form of a powder and the active ingredient is added to the chewing gum formulation by dry blending the active ingredient and the chewing gum formulation). This means that in the final chewing gum tablet, most of the active ingredient is disposed in the spaces between the particles of the chewing gum formulation and/or loosely bound to the outside surfaces of the particles of chewing gum formulation. When the chewing gum tablets are chewed, the outside surfaces of the chewing gum formulation particles are quickly exposed to the saliva in the mouth of the individual chewing the tablet and this leads to a rapid release of the active ingredient to the saliva. This is especially noticeable when the chewing gum tablet dissociates into a multiplicity of pieces upon initial chewing. The release of the active ingredient (i.e., to the saliva of the individual chewing the gum) by the chewing gum tablets of the present invention is substantially faster than the release of the same active ingredient from a chewing gum that was formed by conventional techniques where the active ingredient is added to a melt of the chewing gum and this mixture is then formed into the final chewing gum pieces.

After the active ingredient(s) is(are) added to the chewing gum formulation to form the chewing gum composition, the chewing gum composition, which is in the form of free-flowing particles, is subjected to compression in a tableting machine to form chewing gum tablets. One of the advantages of the chewing gum formulation and composition of the present invention is that it can be directly compressed at high speed (e.g., at tableting speeds of 75,000 tablets per hour or more, preferably from 75,000 to 100,000 tablets per hour) because it does not stick to the punches and dies used in standard high speed tableting machines. These properties are extremely advantageous because they permit the use of the type of high speed tableting machines that are normally used in the pharmaceutical industry to form the chewing gum tablets of the present invention. The use of such tableting machines is advantageous because the pharmaceutical manufacturer will not have to invest in new equipment to produce the chewing gum tablets of the present invention. Further, the production of the chewing gum tablets at high speed in such tableting machines results in cost-savings because the time required to produce a given amount of chewing gum tablets is far less than with the low output machines that are necessary to produce tablets with other gum formulations.

Any active ingredient can be used with the chewing gum formulations of the present invention as long as that active ingredient can be administered orally and does not react adversely with the other components in the chewing gum formulation. Examples of suitable active ingredients are analgesic substances, anti-inflammatory substances, antacid substances, antibiotic substances, decongestant substances, cough suppressant substances, vitamins, stimulants, anaesthetic substances and antiseptic substances. Preferred active ingredients include acetaminophen, ibuprofen, vitamins, antacids, decongestants, cough suppressants, caffeine, nicotine, glucosamine, chondroitin, phaseolamin, benzocaine and lidocaine.

In certain embodiments of the present invention, the chewing gum tablets have a coating that can be composed of at least one layer. The coating can contain at least one sweetener and/or at least one active ingredient. In one embodiment of the present invention, the chewing gum tablet has a coating that contains a sweetening agent that is the only sweetening agent present in the chewing gum tablet. In another embodiment of the present invention, the coating contains at least one active ingredient that is the only active ingredient present in the chewing gum tablet. In a further embodiment of the present invention, the chewing gum tablet has a coating that contains a sweetening agent that is in addition to a sweetening agent that is contained in the remainder of the tablet. In yet another embodiment of the present invention, the chewing gum tablet has a coating that contains an active ingredient that is in addition to an active ingredient that is contained in the remainder of the tablet. In these latter two embodiments of the present invention, the additional sweetening agent or active ingredient that is contained in the coating may be the same as or different from the sweetening agent or active ingredient that is contained in the remainder of the chewing gum tablet.

DETAILED DESCRIPTION OF THE PREFERRED EMBODIMENT(S)

In a preferred embodiment of the present invention, the gum base, granulating agent and at least one processing aid are mixed together in a heated mixer that is outfitted with one or more choppers. The mixer is preheated to a temperature from about 85 to 120° F., preferably from 90 to 110° F., and then the granulating agent is added to the mixer, preferably as a dry powder. The amount of granulating agent used in the chewing gum formulation is usually in the range of from 10 to 90.9% by weight, preferably from 45 to 90.9% by weight, more preferably from 55 to 85% by weight, most preferably from 60 to 80% by weight, of the chewing gum formulation. A portion of the processing aid may be added simultaneously with the granulating agent or shortly after the addition of the granulating agent. The total amount of processing aid used in the chewing gum formulation is usually in the range of from 0.1 to 5% by weight, preferably from 0.5 to 3% by weight, of the chewing gum formulation. The portion of the processing aid added at this stage of the process is usually from ¼ to ¾ of the total amount of processing aid to be added to the chewing gum formulation. After the granulating agent and the first portion of the processing aid is charged to the mixer, the mixer is started and the granulating agent and processing aid are allowed to mix for a short period of time, preferably from 30 seconds to 5 minutes, before the chopper(s) are started. Shortly after the chopper(s) are started, the gum base is added to the mixer. The gum base is used in an amount of from about 9 to 50% by weight of the chewing gum formulation, preferably from 15 to 35% by weight, most preferably from 18 to 30% by weight. The granulating agent, processing aid and gum base are then mixed with the chopper(s) turned on for several minutes while heat is applied to the mixer until the temperature in the mixer reaches about 130 to 150° F., preferably from 135 to 145° F. At that time, the heat applied to the mixer is turned off while the mixing continues with the chopper(s) on. Once the temperature in the mixer reaches about 140 to 160° F., preferably from 145 to 155° F., the chopper(s) is(are) turned off and the second portion of the processing aid is added to the reactor. The mixing is continued for about 1 to 4 minutes, preferably from 1.5 to 3 minutes, with the chopper(s) turned off, after the second portion of the processing aid is added to the mixer. The mixing elements of the mixer are then turned off and the mixture is removed from the reactor, usually as a free-flowing particulate wherein at least 60% by weight of the particles are within a relatively narrow particle size range of from 190 to 420 mm, preferably from 250 to 400 mm.

The ratio of gum base to processing aid can have an effect on the properties of the chewing gum formulation. Generally, as the ratio of the gum base to the processing aid increases, the chewing gum formulation becomes more sticky. Further, as the ratio decreases, the chewing gum formulation becomes less sticky and, at some point, the chewing gum formulation begins to lose its cohesiveness and can fall apart under gentle shear forces. Accordingly, to maintain a desired level of cohesiveness while avoiding stickiness, the ratio of gum base to processing aid should be kept within a predetermined range. For most of the chewing gum formulations of the present invention, the desired ratio of gum base to processing aid is from about 3 to 500. In some embodiments of the present invention, the ratio is from 3 to 250. In other embodiments, the ratio is from 10 to 100 or even 10 to 50.

A preferred granulating agent for use in the chewing gum formulation of the present invention is a polyol such as sorbitol, mannitol and/or isomalt.

A preferred sweetening agent for use in the chewing gum formulation of the present invention is a polyol such as sorbitol, mannitol and/or isomalt.

In a preferred embodiment of the present invention, the chewing gum formulation contains from 45 to 90.9% by weight of sorbitol as the sweetening agent and granulating agent.

A preferred gum base for use in the chewing gum formulation of the present invention is Artica-T (produced by Cafosa Gum SA, Barcelona, Spain).

A preferred processing aid for use in the chewing gum formulation of the present invention is silica gel (e.g., Syloid 244FP, produced by W. R. Grace & Co., Columbia, Md).

It is preferred that the chewing gum formulation is formed from dry particulate materials that contain little or no water so that the chewing gum formulation contains less than 2% by weight water.

When a chewing gum composition is produced, it is also preferred that the active ingredient(s) and any flavoring agents or other excipients that are added to the chewing gum formulation contain little or no water so that the final chewing gum composition that is subjected to tableting contains less than 2% by weight water.

When a chewing gum composition is formed from the chewing gum formulation of the present invention, the chewing gum formulation is usually from 25 to 99% by weight, preferably from 40 to 95% by weight, most preferably from 50 to 80% by weight, of the chewing gum composition.

The chewing gum formulation of the present invention demonstrates superior flow properties in comparison to known compressible chewing gums. These superior flow properties should result in low variability in the weight of tablets produced from the chewing gum formulation and a more uniform active ingredient content in the tablets. Moreover, the chewing gum formulation of the present invention demonstrates enhanced compaction properties when the formulation is directly compressed at high speed on standard tableting machines., Further, the chewing gum formulation of the present invention is produced (i.e., by the process of the present invention) as a free-flowing particulate wherein the particles do not form any strong bonds to each other even during extended storage periods (e.g., several months) at room temperature. Any agglomerates that do form upon production or during storage of the chewing gum formulation are easily broken up by mild comminution techniques (i.e., the agglomerates are very friable) at room temperature.

The process of the present invention permits the production of chewing gum tablets containing active ingredients wherein the active ingredients are never exposed to elevated or depressed temperatures (i.e., temperatures that are significantly above or below normal room temperature). For example, in the process of the present invention, it is unusual for the active ingredient to be exposed to a temperature above 100° F. or below 40° F. In the preferred embodiments of the present invention, the active ingredient is only exposed to temperatures in the range from 50° F. to 90° F. during the production of the chewing gum tablets. In the most preferred embodiments of the present invention, the active ingredient is only exposed to temperatures in the range from 50° F. to 80° F. during the production of the chewing gum tablets. Accordingly, the process of the present invention is highly desirable when the active ingredient of interest is sensitive to elevated or depressed temperatures.

As discussed above, it is desirable for the chewing gum tablet of the present invention to quickly dissociate into a multiplicity of small pieces upon initial chewing followed by a reformation of the pieces into a coherent mass of chewing gum after a few seconds of active chewing. However, it is not necessary that the chewing gum tablets of the present invention demonstrate this property or behavior. In certain embodiments of the present invention (e.g., where the amount of gum base is greater than 25% by weight of the chewing gum formulation), the chewing gum tablets may only dissociate into two pieces upon initial chewing followed by a rapid reformation of the pieces into a coherent mass of chewing gum after a small number of additional chews (e.g., 1 to 5 additional chews). Still further, in certain embodiments of the present invention, the chewing gum tablet may not actually dissociate at all during the initial chew but may instead form a single coherent body that has many cracks or fissures after the initial chew, which cracks and fissures permit the saliva of the individual chewing the gum to thoroughly wet the interior of the tablet before the cracks and fissures close up after several additional chews.

The following examples embody the invention and preferred embodiments of the invention, but should not be interpreted as a limitation on the scope of the invention.

EXAMPLE 1

A chewing gum formulation according to the present invention was produced as set forth below.

The mixer used was a Littleford FM 1200 mixer (volume 1200 liters, available from Littleford Day, Ky., USA) with plough blades. The mixer had two feed ports, one exit port and four choppers located on the bottom of the mixer. The mixer was equipped with a steam jacket and had thermometers or thermocouples measuring the temperature of the steam jacket and the temperature of the inside of the mixer.

The jacket temperature of the mixer was initially set to 160 to 165° F. Once the temperature in the mixer reached 95 to 105° F., the mixer was charged with 284.4 kg of sorbitol powder (SORBOGEM™ 712 produced by SPI Polyols, Inc. of New Castle, Del.) and 1.8 kg of silica gel (SYLOID® 244FP, produced by W. R. Grace & Co., Grace Davidson, Columbia, Md.). The mixer was then started with the plough blades running at 130 rpm. The sorbitol and silica gel were mixed for one minute before the choppers were turned on. Shortly after the choppers were turned on, 72 kg of gum base (ARTICA-T, produced by Cafosa Gum SA, Barcelona, Spain) were added to the mixer and the sorbitol, silica gel and gum base were mixed until the temperature in the mixer reached 140° F. (about 15 minutes after the gum base was added), at which time the steam to the jacket was turned off. The mixing continued until the temperature in the mixer reached about 150° F. (about 17 minutes after the gum base was added), at which time the choppers were turned off and another 1.8 kg of silica gel (SYLOID® 244FP, produced by W. R. Grace & Co., Grace Davidson, Columbia, Md.) was added to the mixer. The mixing was continued with the choppers turned off for about two minutes after the second portion of the silica gel was added to the mixer. The contents of the mixer (i.e., the chewing gum formulation) were then emptied into drums by opening the exit port and allowing the chewing gum formulation, in particulate form, to fall from the mixer into the drums.

EXAMPLE 2

A chewing gum composition according to the present invention was produced as set forth below using calcium carbonate as the active ingredient (as an antacid).

A 60 inch SWECO sifter equipped with a 16 mesh screen was prepared and cleaned.

1617.0 kg of chewing gum formulation (obtained from multiple batches which were each produced by the method described in Example 1) was screened through the sifter. A small amount of chewing gum formulation was retained on the 16 mesh screen (less than 10% by weight of the chewing gum formulation). This retained material was fed to a Fitz mill with a 0.078 to 0.125 drilled hole screen, milled in the Fitz mill and then added to the chewing gum formulation that had passed through the 16 mesh screen. It should be noted that the Fitz mill step was performed solely to maximize the use of the chewing gum formulation and was not necessary to provide the chewing gum formulation as a free-flowing particulate. The small amount of chewing gum formulation that was retained on the 16 mesh screen can simply be discarded without effecting the properties of the chewing gum formulation or the chewing gum composition produced from the chewing gum formulation.

190.0 kg of calcium carbonate (GRAN CAL CARB LL USP, Product Code G-0108/P0287-01, produced by Delavau, Philadelphia, Pa., USA) was also screened through the sifter.

A preblend of 100.0 kg of crystalline xylitol (Xylitol C, Cultor, Ardsley, N.Y.), 3.0 kg of aspartame (Aspartame Nutrasweet, August, Ga.), 20.0 kg of citric acid monohydrate (Citric Acid from Roche, Pineville, N.C.), 10.0 kg of strawberry flavor (#915.005/EN, from Flavors Of North America, Chicago, Ill., USA), 10.0 kg of mixed fruit flavor (#852.392/EN, from Flavors Of North America, Chicago, Ill., USA) and 10.0 kg of masking flavor (#936.471/EN, from Flavors Of North America, Chicago, Ill., USA) was prepared by adding the components to a clean container (i.e., a fiber drum) and then rolling the container on the floor by hand for about one minute.

The above-described preblend was then screened through the sifter.

The following components were then charged to a double cone blender (Patterson Kelly 100, East Stroudsberg, Pa.) with a volume of 100 cubic feet in the order and amounts shown below. Each component was passed through a ¼ inch screen at the receiving hopper and then passed over magnets (to remove any metal that may be present) as it entered the blender.

1) About one-half of the 1617.0 kg of screened chewing gum formulation.
2) All of the screened preblend.
3) All of the calcium carbonate.
4) The remainder of the screened chewing gum formulation.

The blender lid was then secured and the blender was turned on at 8 rpm for 15 minutes.

In a separate step, 20 kg of talc (Talc 140 from Mutchler, Westwood, N.J.) and 20.0 kg of magnesium stearate (from Mallinckrodt, St. Louis, Mo.) were added to a clean drum which was then rolled by hand on the floor for about one minute.

After the initial 15 minute mixing step, the mixture of the talc and the magnesium stearate was added to the blender and the contents of the blender were mixed for another 5 minutes at 8 rpm.

After this additional 5 minute mixing period, the contents of the blender (i.e., the chewing gum composition) were discharged as a free-flowing particulate into drums.

The chewing gum composition can be directly compressed at high speed on a high speed tableting machine, such as those made by Killian or Korsh, capable of producing at least 75,000 tablets per hour, to form cylindrical tablets having the following dimensions: 19.1 mm circular diameter and 8.8 mm thick. Each tablet weighed about 2.8 grams and contained about 250 mg of calcium carbonate as the active ingredient (i.e., an antacid).

One or more liquid flavoring agents (e.g., flavoring agents contained in one or more oils or alcohols as the carrier) can be added to the chewing gum formulation or composition during or after the production of the chewing gum formulation or composition. In one embodiment of the present invention, the liquid flavoring agent(s) is or are added to the chewing gum formulation (i.e., before the addition of the active ingredient). In another embodiment of the present invention, the liquid flavoring agent(s) is or are added to the chewing gum composition after the addition of the active ingredient. The total amount of liquid flavoring agent(s) added to the chewing gum formulation or composition is usually from 0.1% to 3% by weight of the formulation or composition. Preferably, the total amount of liquid flavor added is from 1 to 2% by weight of the formulation or composition. One of the benefits of adding a liquid flavoring agent to the chewing gum formulation or composition is that the final chewing gum product has an increased plasticity giving the product a softer (more gum-like) texture. Some additional benefits of using a liquid flavoring agent are increased flexibility in the production and processing of the chewing gum formulation and/or composition and a greater range of flavors that can be incorporated into the final product.

What is claimed is:

1. A method of producing a chewing gum tablet comprising a chewing gum formulation and at least one active ingredient, wherein the chewing gum tablet dissociates into at least two pieces upon initial chewing followed by a reformation of the pieces into a coherent mass after additional chewing, comprising the steps of:
   (a) dry mixing a gum base, a granulating agent and at least one processing aid to form a chewing gum formulation that contains less than 2% by weight water;
   (b) adding one or more additional ingredients, including an active ingredient, to the chewing gum formulation to form a chewing gum composition in the form of a free-flowing particulate that contains less than 2% by weight water; and
   (c) directly compressing the chewing gum composition into said chewing gum tablet;
wherein the gum base is in the form of particles and during the dry mixing step, the temperature of the gum base is raised to an elevated temperature where at least the outer surfaces of the gum base particles melt and further wherein a portion of the processing aid is mixed with the gum base and granulating agent before the temperature is raised to said elevated temperature and at a first temperature that is below the melting point of the gum base and, after the temperature of the gum base is raised to said elevated temperature, mixing continues until a uniform mixture of the gum base, the granulating agent and the processing aid is obtained in the form of particles of said uniform mixture, at which time, the temperature of the gum base is reduced to a point that is below the melting point of the gum base and the remainder of the processing aid is added to and mixed with the particles of said uniform mixture until the remainder of the processing aid forms a partial coating on the outer surfaces of the particles of said uniform mixture.

2. The method of claim 1, wherein after the chewing gum formulation is produced, it is maintained at temperatures in the range of 68 to 86° F. at all times before the tableting step.

3. The method of claim 1, wherein in step (a), at least one sweetening agent is dry mixed with the gum base, granulating agent and at least one processing aid to form said chewing gum formulation.

4. The method of claim 1, wherein in step (b), said additional ingredients are selected from the group consisting of sweetening agents, active ingredients, flavoring agents, coloring agents and lubricants.

5. The method of claim 1, wherein the granulating agent is also a sweetening agent.

6. The method of claim 1, wherein the granulating agent is water-soluble.

7. The method of claim 1, wherein the processing aid is selected from the group consisting of silica substances and silicate substances.

8. The method of claim 1, wherein the processing aid is selected from the group consisting of talc, silica gel, precipitated silica, fumed silica and colloidal silica.

9. The method of claim 1, wherein the granulating agent is a sugar or a polyol.

10. The method of claim 1, wherein the granulating agent is sorbitol.

11. The method of claim 1, wherein the granulating agent is mannitol, isomalt or mixtures thereof.

12. A method of producing a chewing gum tablet comprising a chewing gum formulation and at least one active ingredient, wherein the chewing gum tablet dissociates into at least two pieces upon initial chewing followed by a reformation of the pieces into a coherent mass after additional chewing, comprising the steps of:
   (a) dry mixing a gum base, a granulating agent and at least one processing aid to form a chewing gum formulation that contains less than 2% by weight water;
   (b) adding one or more additional ingredients, including an active ingredient, to the chewing gum formulation to form a chewing gum composition in the form of a free-flowing particulate that contains less than 2% by weight water; and
   (c) directly compressing the chewing gum composition into said chewing gum tablet;
wherein the gum base is in the form of particles and during the dry mixing step, the temperature of the gum base is raised to an elevated temperature where at least the outer surfaces of the gum base particles melt, and further wherein a portion of the processing aid is mixed with the gum base and granulating agent before the temperature is raised to said elevated temperature and at a first temperature that is below the melting point of the gum base and, after the temperature of the gum base is raised to said elevated temperature, mixing continues until a uniform mixture of the gum base, the granulating agent and the processing aid is obtained in the form of particles of said uniform mixture, at which time the remainder of the processing aid is added to and mixed with the particles of said uniform mixture until the remainder of the processing aid forms a partial coating on the outer surfaces of the particles of said uniform mixture.

13. The method of claim 12, wherein after the chewing gum formulation is produced, it is maintained at temperatures in the range of 68 to 86 °F at all times before the tableting step.

14. The method of claim 12, wherein in step (a), at least one sweetening agent is dry mixed with the gum base, granulating agent and at least one processing aid to form said chewing gum formulation.

15. The method of claim 12, wherein in step (b), said additional ingredients are selected from the group consisting of sweetening agents, active ingredients, flavoring agents, coloring agents and lubricants.

16. The method of claim 12, wherein the granulating agent is also a sweetening agent.

17. The method of claim 12, wherein the granulating agent is water-soluble.

18. The method of claim 12, wherein the processing aid is selected from the group consisting of silica substances and silicate substances.

19. The method of claim 12, wherein the processing aid is selected from the group consisting of talc, silica gel, precipitated silica, fumed silica and colloidal silica.

20. The method of claim 12, wherein the granulating agent is a sugar or a polyol.

21. The method of claim 12, wherein the granulating agent is sorbitol.

22. The method of claim 12, wherein the granulating agent is mannitol, isomalt or mixtures thereof.

* * * * *